United States Patent [19]
Walker, Jr. et al.

[11] Patent Number: 5,338,881
[45] Date of Patent: Aug. 16, 1994

[54] PROCESS FOR PREPARING DIKETONES

[75] Inventors: Theodore R. Walker, Jr.; Winston J. Jackson, Jr.; Jean C. Fleischer, all of Kingsport, Tenn.

[73] Assignee: Eastman Chemical Company, Kingsport, Tenn.

[21] Appl. No.: 556,677

[22] Filed: Jul. 23, 1990

[51] Int. Cl.$^5$ .............................................. C07C 59/76
[52] U.S. Cl. .................................... 562/462; 562/426; 562/429; 562/460; 562/459; 562/461; 562/466; 562/467; 562/473
[58] Field of Search .............. 562/426, 429, 460, 461, 562/462, 466, 467, 473

[56] References Cited

U.S. PATENT DOCUMENTS

| | | | |
|---|---|---|---|
| 3,767,620 | 10/1973 | Angelo et al. | 260/47 |
| 4,453,010 | 6/1984 | Staniland | 568/319 |
| 4,611,033 | 9/1986 | Maresca | 525/419 |
| 4,816,556 | 3/1989 | Gay et al. | 528/176 |

FOREIGN PATENT DOCUMENTS 135224 8/1984 Japan.
2116990 10/1983 United Kingdom.

OTHER PUBLICATIONS

M. Ueda et al., *Makromol.*, 20, pp. 2675–2678 (1987).
M. Ueda et al., *Makromol. Chem., Rapid Commun.*, 5, pp. 833–836 (1985).
UEDA, Metal Macromolecules 20(11) 2675–8 1987.

*Primary Examiner*—Paul J. Killos
*Attorney, Agent, or Firm*—Betty J. James

[57] ABSTRACT

This invention concerns a process for preparing diketones and keto-acids by reacting a dicarboxylic acid and an aromatic compound in the presence of an alkylsulfonic acid such as methanesulfonic acid and a phosphorus pentoxide. The diketones and keto-acids can be used to prepare polyketones which are useful as molding plastics, coatings, films, fibers, and the like.

22 Claims, No Drawings

PROCESS FOR PREPARING DIKETONES

FIELD OF INVENTION

This invention relates to a process for preparing diketones and keto-acids by reacting a dicarboxylic acid and an aromatic compound in the presence of an alkylsulfonic acid and phosphorus pentoxide.

BACKGROUND OF THE INVENTION

In many prior art processes for preparing diketones, the diketones are minor by-products or the diketones are prepared by commercially impractical circuitous routes. Some diketones are reported to be prepared by well-known Friedel-Crafts reactions using diacid chlorides and such catalysts as $AlCl_3$. An example is contained in U.S. Pat. No. 4,816,556 which describes preparation of two diketones by reaction of 2 moles of diphenyl ether with 2 moles terephthalyl chloride (or 2 moles isophthalyl chloride) with 4 moles aluminum chloride as catalyst. Some disadvantages of this process are high cost which results from (1) the use of expensive diacid chlorides instead of diacids and (2) the use of large amounts of catalyst which is destroyed in the workup. Disposal of large amounts of aluminum wastes and corrosion from HCl by-product could also present problems. Another prior art process discloses preparation of a diketone from isophthalic acid and anisole. This process is disclosed by Mitsuru Ueda and Masaki Sato, Makromol. 20, pp. 2675–2678 (1987). This diketone is not the type of this invention since it cannot be polymerized to give a polyketone. The reaction medium was PPMA, which is a mixture of phosphorus pentoxide and methanesulfonic acid, at a particular weight ratio. The phosphorus pentoxide acts as a dehydrator in that it takes up the water that is a product of the reaction and is itself converted to phosphorus acids. This publication also reports the preparation of polyketones by reaction of aromatic diacids containing ether linkages with aromatic compounds containing ether linkages. The authors state that "typical dicarboxylic acids, such as isophthalic acid and terephthalic acid, cannot be used."

Another prior art publication which may be relevant to the present invention is Mitsuru Ueda and Toshiya Kano, Makrol. Chem., Rapid Commun., 5, pp. 833–836 (1985). This paper reports preparation of the following diketone in PPMA under specific reaction conditions:

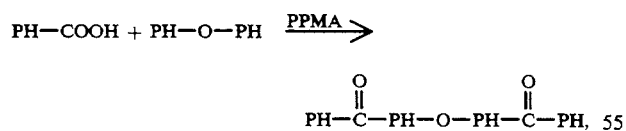

wherein PH is phenyl. This publication also reports the preparation of polymers from aliphatic diacids and difunctional aromatic compounds. Isophthalic acid did not give polymers, only low oligomer. No work with terephthalic acid was reported.

Another publication which may be relevant to the present invention is U.S. Pat. No. 4,453,010. This patent discloses the preparation of aromatic hydroxyketones in methanesulfonic acid without a dehydrator such as phosphorus pentoxide. An aromatic acid reacts with a hydroxy-containing aromatic compound to give a hydroxyketone.

None of the above publications disclose preparation of a keto-acid.

It would be highly desirable to have a process for preparing diketones and keto-acids that overcomes the problems of prior art processes.

SUMMARY OF THE INVENTION

The process of the present invention overcomes disadvantages of the prior art. The process of the present invention can be described as a process for producing a diketone or keto-acid compound comprising contacting (A) at least one aromatic dicarboxylic acid containing 8 to 30 carbon atoms with (B) at least one polynuclear aromatic compound containing 10 to 30 carbon atoms, in the presence of at least one solvent, phosphorus pentoxide, and at least a catalytic amount of at least one alkylsulfonic acid containing 1 to 4 carbon atoms, under conditions to promote formation of the desired diketone or keto-acid compound.

A preferred process of the invention can be described as a process for producing a diketone or keto-acid compound comprising contacting (A) at least one compound selected from the group consisting of terephthalic acid, chloroterephalic acid, 5-methylisophthalic acid, isophthalic acid, 4,4'-biphenyldicarboxylic acid, 4,4'-stilbenedicarboxylic acid, 4,4'-oxydibenzoic acid, 1,3-naphthalenedicarboxylic acid, 1,5-naphthalenedicarboxylic acid, 1,6-naphthalenedicarboxylic acid, 1,7-naphthalenedicarboxylic acid, 2,5-naphthalenedicarboxylic acid, 2,6-naphthalenedicarboxylic acid, and 2,7-naphthalenedicarboxylic acid, with (B) at least one compound selected from the group consisting of diphenyl ether, diphenyl sulfide, biphenyl, naphthalene, anthracene, fluorene, xanthane, and phenanthrene in the presence of at least one solvent, phosphorus pentoxide, and at least a catalytic amount of at least one alkylsulfonic acid containing one to four carbon atoms, at a temperature of about 0° to 100° C. for a time sufficient to form the desired diketone or keto-acid compound.

DETAILED DESCRIPTION OF THE INVENTION

The diketones and keto-acids produced according to this invention are useful as monomers for high heat- and chemical-resistant polyketones. These polyketones are useful as molding plastics, coatings, films, fibers, matrix resins, and the like. The diketone or keto-acid made by the process of the present invention is produced as HOH (i.e., water) is formed by the elimination of an OH group from a carboxylic acid and an H from hydrogen attached to an aromatic ring. Thus, in the case of diketone, the diacid becomes linked to two aromatic rings through its two carbonyl groups. In the case of keto-acid, the diacid becomes linked to one aromatic ring.

As is readily apparent, reactant (B) (that is, the aromatic compound) is not a dicarboxylic acid. Illustrative diketones and keto-acids produced by the process according to this invention include the following:

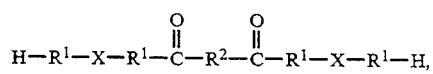

-continued

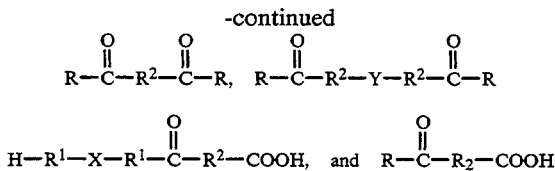

wherein each $R^1$ is, independently, (a) a phenylene moiety optionally substituted with up to three substituents selected from the group consisting of lower alkyl and lower alkoxy, (b) a naphthylene moiety optionally substituted with up to six substituents selected from the group consisting of lower alkyl and lower alkoxy, or (c) a biphenylene moiety optionally substituted with up to eight substituents selected from the group consisting of lower alkyl and lower alkoxy, each $R^2$ is, independently, (a) a phenylene moiety optionally substituted with up to three substituents selected from the group consisting of lower alkyl, lower alkoxy, halo, hydroxy, acyl, perfluoroalkyl, cyano, nitro, dialkylamino, and acylamino, (b) a naphthylene moiety optionally substituted with up to six substituents selected from the group consisting of lower alkyl, lower alkoxy, halo, hydroxy, acyl, perfluoroalkyl, cyano, nitro, dialkylamino, and acylamino, or (c) a biphenylene moiety optionally substituted with up to eight substituents selected from the group consisting of lower alkyl, lower alkoxy, halo, hydroxy, acyl, perfluoroalkyl, cyano, nitro, dialkylamino, and acylamino.

X is a direct bond, O, S, or —CH=CH—;

Y is a direct bond, O, S,

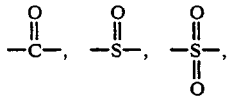

—CH=CH— or —O—$R^2$—O—; and

R is the residue of a polynuclear hydrocarbon after removal of a hydrogen atom and contains at least 10 carbon atoms (i.e., is a residue of reactant (B)).

As used herein the term "halo" refers to chloro, bromo, fluoro, or iodo; the term "lower alkyl" refers to alkyl groups having 1 to 10 carbon atoms; the term "lower alkoxy" refers to alkoxy groups having 1 to 10 carbon atoms; the term "acyl" refers to acyl groups having 1 to 10 carbon atoms; the term "perfluoroalkyl" refers to perfluoroalkyl groups having 1 to 10 carbon atoms; the term "dialkylamino" refers to dialkylamino groups wherein each alkyl moiety has 1 to 10 carbon atoms; and the term "acylamino" refers to acylamino groups having 1 to 10 carbon atoms. Preferred halo groups are iodo and fluoro; preferred lower alkyl groups are methyl, ethyl, propyl and isopropyl; preferred lower alkoxy groups are methoxy, ethoxy, propyloxy and 1-methylethoxy; preferred acyl groups have 1 to 4 carbon atoms; preferred perfluoroalkyl groups have 1 to 4 carbon atoms; preferred dialkylamino groups are wherein each alkyl moiety has 1 to 4 carbon atoms; and preferred acylamino groups have 1 to 4 carbon atoms. The optional substituents of the $R^1$ and $R^2$ groups may be the same or different.

The aromatic dicarboxylic acids (reactant (A)) which are useful in the process of the invention may contain 8 to 30 carbon atoms and include all of those disclosed in British Patent 2,166,990. Additionally, other aromatic dicarboxylic acids which are not disclosed in British Patent 2,166,990 are also useful in the process of the invention. Such dicarboxylic acids include those having the general formula HOOC—$R^2$—COOH, where —$R^2$— is as defined hereinabove and the —COOH moieties are directly bonded to an aromatic ring and are separated from each other by at least three carbon atoms. Other suitable dicarboxylic acids have the general formula HOOC—$R^2$—Y—$R^2$—COOH wherein —Y— and —$R^2$—, independently, are as defined hereinabove. It is preferred that the aromatic moiety or moieties are unsubstituted.

Examples of aromatic dicarboxylic acids which may be used as reactant (A) include the following:

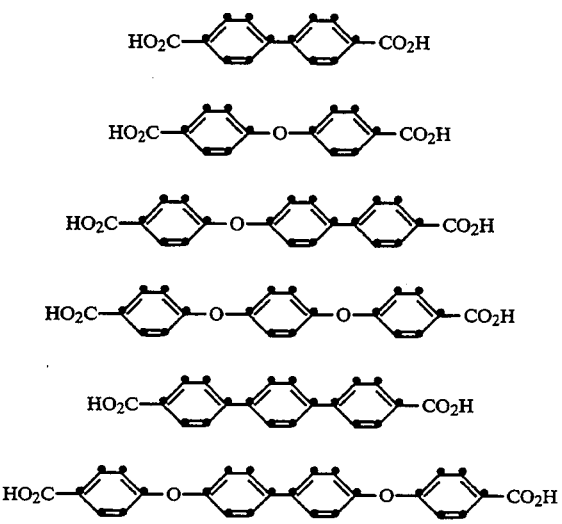

Preferred aromatic dicarboxylic acids include terephthalic acid, chloroterephthalic acid, 5-methylisophthalic acid, isophthalic acid, 4,4'-biphenyldicarboxylic acid, 4,4'-oxydibenzoic acid, 4,4'-stilbenedicarboxylic acid, 1,3-naphthalenedicarboxylic acid, 1,5-naphthalenedicarboxylic acid, 1,6-naphthalenedicarboxylic acid, 1,7-naphthalenedicarboxylic acid, 2,5-naphthalenedicarboxylic acid, 2,6-naphthalenedicarboxylic acid, and 2,7-naphthalenedicarboxylic acid.

The polynuclear aromatic compounds (reactant (B)) which may be used in the process of the invention may contain 10 to 30 carbon atoms and include all of those disclosed in British Patent 2,116,990 and U.S. Pat. No. 4,611,033, incorporated herein by reference, plus other compounds having the general formulae H—$R^1$—X—$R^1$—H or H—$R^3$—H, wherein each $R^1$, independently and X are as defined hereinabove and $R^3$ is a polynuclear hydrocarbon moiety. Examples of $R^3$ moieties are those having 2, 3 or 4 fused rings, each of which is preferably aromatic, optionally substituted with up to 8 substituents such as with lower alkyl and/or lower alkoxy. Each of the fused rings of the $R^3$ moiety may also optionally contain 1, 2 or 3 hetero atoms such as O, N and/or P. Preferred are unsubstituted, non-heterocyclic $R^3$ moieties wherein all rings are aromatic.

Examples of compounds which may be used as reactant (B) include the following:

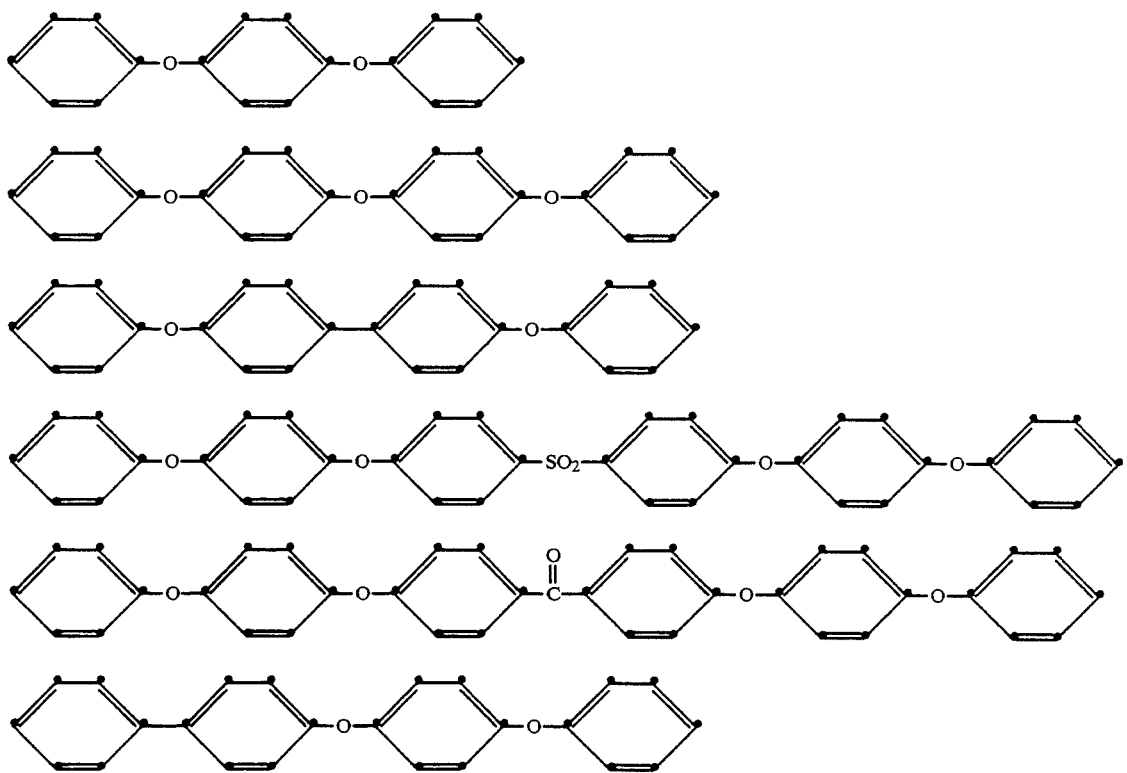

Other suitable compounds which may be used as reactant (B) include compounds such as diphenyl sulfide, fluorene, xanthene, dibenzofuran, thianthrene, phenoxathiin, dibenzo-p-dioxin, diphenylene, biphenyl, 4,4'-diphenoxybiphenyl, 2,2'-diphenoxybiphenyl, 1,2-diphenoxybenzene, 1,4-diphenoxybenzene, 1,3-diphenoxybenzene, 1-phenoxynaphthalene, 1,2-diphenoxynaphthalene, diphenyl ether, 1,5-diphenoxynaphthalene and the like.

Preferred aromatic compounds useful as reactant (B) are diphenyl ether, diphenyl sulfide, biphenyl, naphthalene, anthracene, phenanthrene, fluorene, xanthane, dibenzofuran, and dibenzo-p-dioxin.

The process of the invention is carried out in the presence of an alkylsulfonic acid(s) containing 1-4 carbon atoms and includes methanedisulfonic acid and 1,2-ethanedisulfonic acid. Methanesulfonic acid is preferred because of its commercial availability and its low cost. The alkylsulfonic acid is preferably substantially anhydrous, but small amounts of water can be tolerated. The alkylsulfonic acid acts as a catalyst for the reaction and is therefore present in at least a catalytic amount. However, it is also preferred that the alkylsulfonic acid perform a dual function and act as solvent, in whole or in part, for the process of the invention. The catalytic amount of alkylsulfonic acid is preferably at least about 20 mole % relative to reactant (A). A concentration of about 8 moles of alkylsulfonic acid per mole of desired product formed is preferred, but lesser or higher amounts may be used as dictated by the solubility of the acid and hydrocarbon starting materials and by the practicality of recovering the alkylsulfonic acid for recycle.

In some cases some of the alkylsulfonic acid may be replaced by excess aromatic compound to function as part of the solvent system, with the understanding that the aromatic compounds typically do not dissolve diacids as well as the sulfonic acids do. While some aromatic compounds are soluble in the sulfonic acids, most are not miscible. Therefore, if a large excess of aromatic compound is used, a two-phase system may result. In addition, part of the alkylsulfonic acid may be replaced by other solvents, especially well-known Friedel-Crafts solvents such as chlorinated hydrocarbons, o-dichlorobenzene, nitrobenzene, and nitromethane.

It is an advantage of the present invention that it may be carried out where the aklylsulfonic acid is used in combination with an aromatic dicarboxylic acid of poor solubility in the alkylsulfonic acid, e.g., a solubility of less than 5% by weight in the alkylsulfonic acid. Examples of such diacids of poor solubility include terephthalic acid, 2,6-naphthalenedicarboxylic acid, and 4,4'-biphenyldicarboxylic acid. If the acid of poor solubility is very finely divided, e.g., small enough to pass through a greater than or equal to 250 mesh screen, the process of the invention will proceed particularly well.

The process of the reaction requires the presence of phosphorus pentoxide. Although it is not desired to be bound by any particular theory or mechanism, it is believed that the phosphorous pentoxide acts as a dehydrator to aid in producing an acylium ion from carboxylic acid and to remove the water produced in the reaction. The amount of phosphorus pentoxide used in the reaction should be at least enough to react with all the water produced in the reaction, i.e., one-third mole phosphorus pentoxide for each carboxyl group, but excess may be used. The preferred amount of phosphorus pentoxide is about 1.5 to about 2.5 moles per mole of diacid.

The reaction may be carried out at 0° to 100° C., but temperatures up to 150° C. may be used with some reactants. The higher temperatures give faster reaction rates but also increase the probability of undesirable side reactions, particularly sulfone formation. At temperatures below 50° C. the reaction rates are appreciably slower. A temperature of about 60°–75° C. is preferred.

The time of the reaction may vary from a few minutes to several days, depending, for example, on the structure of the starting materials, the temperature, and the amount of anhydride and sulfonic acid. The optimum conditions for the preparation of the diketones by the process of the invention should be determined by routine experimentation for each. However, at 60°–75° C. most of the reactions are complete in at least about 2 hours, typically in 4–8 hours.

The diacid (reactant (A)), aromatic compound (reactant (B)), phosphorus pentoxide, and alkylsulfonic acid may be mixed in any order. Although excess aromatic hydrocarbon (reactant (B)) may be used in the process, it is not needed for avoidance of oligomer. The presence of oligomer does not interfere with polymerization as long as the amount of it is known so that polymerization may be conducted with the correct stoichiometry. However, excess reactant (B) may cause difficulties in isolation of the product. Since excess reactant (B) increases the rate of reaction, the preferred amount is a small stoichiometric excess of 5–10% relative to reactant (A), but the reaction can be conducted with no excess reactant (B).

The diketones and keto-acids prepared by the process of the invention may be isolated by precipitation in water followed by extraction with an alcohol. The water and alcohol typically remove >99% of the alkylsulfonic acid from the diketone or keto-acid. Residual sulfonic acid and any minor impurities may be removed by recrystallization of the diketone from a solvent. It is usually not necessary to remove small amounts of oligomer that form, since the oligomer will polymerize along with the diketone product to give the desired polyketone. Surprisingly, the highest purity is obtained when the diketone is purified by distillation. Considering the high boiling point of the diketones even under high vacuum (usually >300° C.), it would be expected that distillation would be accompanied by decomposition. However, the diketones exhibit unusual thermal stability.

The alkylsulfonic acid may be recovered for recycling by distilling the aqueous solution to separate water and the sulfonic acid.

Diacids of poor solubility in alkylsulfonic acid are particularly useful because the resulting keto-acid and/or diketone precipitate from the reaction mixture. This lowers the cost of isolating product and eliminates the cost of separating the alkylsulfonic acid from water before recycling. When a mixture of keto-acid and diketone are obtained, they may be separated, if desired, by extraction of the acid with base or by other means. Conditions may be selected to promote the product desired. The more finely divided the diacid starting material, the faster the reaction will go.

When keto-acid is the desired product, it can usually be made simply by using the proper ratio of reactants; that is, a 1:1 ratio of diacid (A) to aromatic hydrocarbon (B). Lower temperatures (25°–50° C.) favor production of the keto-acid by inhibiting reaction of the second less active carboxyl group. Excess diacid (A) may be used since only one ring of the aromatic hydrocarbon reacts significantly under these mild conditions. For each keto-acid, the reaction should be followed by an analytical method to determine the reaction time needed.

The diketone formed by the process of the invention is typically formed with production of only small amounts of oligomer. It is not desired to be bound by any particular theory or mechanism; however, it is believed that when a carbonyl of the diacid is attached to one ring of the aromatic compound, the other ring(s) of the aromatic compound is then sufficiently deactivated to inhibit reaction with a carboxyl group.

The diketone may then be converted to a polyketone under more reactive conditions. For example, one gram-mole of diketone and one gram-mole of a diacid chloride in a reaction catalyzed by $AlCl_3$ in a dichlorobenzene solvent will produce a polyketone. Unstable cyclic alcohol end-groups, such as described in U.S. Pat. No. 3,767,620, cannot occur. In the diketone structure as follows:

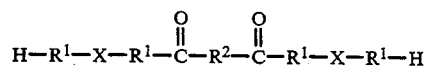

only the terminal aromatic rings can react with the acid chloride. The internal rings are deactivated by the carbonyls. If the acid chloride reacts at the ortho position of a terminal aromatic ring, it cannot further react with the nearby (but deactivated) internal ring to produce thermally-unstable cyclic alcohol, such as is described in U.S. Pat. No. 3,767,620. In addition, if a dicarboxylic acid component different from that used in making the diketone is used for preparing the polyketone, a uniform alternating structure can be produced.

Keto-acid may also be polymerized to polyketone under more reactive conditions, such as a reaction medium of triflic acid/phosphorus pentoxide, or the keto-acid may be converted to keto-acid chloride and polymerized with well-known Friedel-Crafts catalysts such as $AlCl_3$. Unstable cyclic alcohol cannot be produced during the polymerization for the same reason that it could not be produced when diketone was polymerized. The keto-acid, like diketone, had been purified to remove all non-para isomers. Ortho isomers can cyclize, para cannot.

A keto-acid is stoichiometrically correct. It does not require the addition of another monomer for polymerization. However, copolymers may be produced by polymerizing two or more keto-acids or by polymerizing a keto-acid, a diketone, and enough diacid to balance the stoichiometry.

In the reaction of an aromatic hydrocarbon with a diacid to produce diketone, it is not necessary that the reaction go to completion. A mixture of diacid, keto-acid, and diketone is suitable for polymerization. It is only necessary that enough aromatic hydrocarbon is reacted to produce ketone, so that more aromatic compound will not need to be added during the polymerization. To get the proper stoichiometry, diacid (which may or may not be the same diacid) is added but not aromatic hydrocarbon. The reason for not adding aromatic hydrocarbon to the polymerization mixture is that ketone isomers can occur which may cyclize to form unstable units. For example,

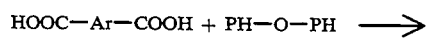

-continued

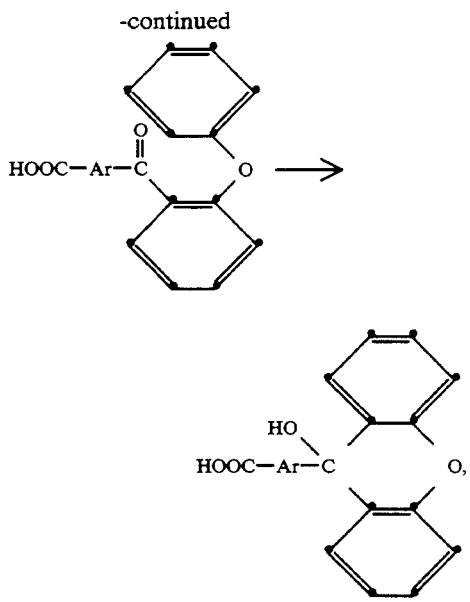

wherein PH is phenyl and Ar is an aromatic moiety.

When diketones or keto-acids are made, such "ortho" isomers that may cyclize are typically removed during purification. During polymerization "ortho" substitution can occur but cyclization cannot because the adjacent ring has been deactivated by a carbonyl.

Before polymerizing a product mixture of diacid, keto-acid, and diketone, the exact amount of each component should be determined. A convenient method of doing this is high-pressure liquid chromatography (HPLC), which gives an accurate weight % of each component.

The following examples are submitted for a better understanding of the invention, but should not be construed as a limitation thereon. In the examples the reactions were followed by field desorption mass spectrometry (FDMS) to determine when the reactions were complete.

Product identifications were made by FDMS and nuclear magnetic resonance (NMR).

EXAMPLE 1

This example illustrates the process for producing a diketone.

Methanesulfonic acid, 192 g (2.0 moles), is heated to 80°–85° C. in a 500-mL, 3-neck reaction flask with stirring, and 28.4 g (0.2 mole) phosphorus pentoxide is added. When solution is virtually complete, 33.2 g (0.2 mole) isophthalic acid is added and the stirring mixture is cooled to about 70° C. Diphenyl ether, 75 g (0.42 mole), is added in one portion and the mixture is stirred for 4 hours at 70°–75° C. The mixture is cooled to room temperature and poured into a dropping funnel. A mixture of 375 mL of 2-ethoxyethanol and 125 mL of water is stirred and heated at 70°–75° C. in a 2-L, 3-neck flask. The reaction mixture is added dropwise from the dropping funnel to the aqueous mixture which is stirring vigorously. The temperature is maintained at 65°–80° C. throughout the addition. Afterwards the heat is cut off and the mixture is allowed to cool to room temperature with stirring. The solid precipitate is collected and washed first with water, then with a small amount of chilled methanol. This procedure gives 81 g (86% yield) of 1,3′-bis(4-phenoxybenzoyl)benzene.

EXAMPLE 2

This example illustrates the process for making a diketone from biphenyl.

Methanesulfonic acid, 480.5 g (5.0 moles), is heated to 80°–85° C. in a 1-L reaction flask with stirring and 56.8 g (0.4 mole) phosphorus pentoxide is added. Isophthalic acid, 66.4 g (0.4 mole), is added and the temperature is lowered to 70°–75° C. where it is maintained throughout the reaction period. Biphenyl, 135.6 g (0.88 mole), is added portionwise. After 3.5 hours reaction time, the mixture is poured into 800 mL of stirring cold water. The precipitate is collected, washed thoroughly with water, and dried. The yield of 1,3-bis(4-phenylbenzoyl)benzene is 170 g (97% yield). The product may be further purified by recrystallization from a solvent such as 2-ethoxyethanol.

EXAMPLE 3

This example illustrates the preparation of a diketone from a diacid of very low solubility in methanesulfonic acid.

Terephthalic acid, 8.3 g (0.05 mole), 96 mL (1.0 mole) methanesulfonic acid, 19.5 g (0.115 mole) diphenyl ether, and 28.4 g (0.2 mole) phosphorus pentoxide are mixed and heated at 80°–85° C. After one hour about 50% of the terephthalic acid has reacted; after four hours 77% has reacted. The product is diketone containing small amounts of tetraketone oligomer and methyl sulfone. No significant amount of keto-acid is produced. After cooling the reaction mixture to 25° C., the precipitate is collected, washed with methanesulfonic acid, and washed with water. To remove unreacted terephthalic acid, the solids are stirred for 2 hours in 300 mL of 10% aqueous KOH.

EXAMPLE 4

This example illustrates the value of using finely divided diacid when the diacid has very low solubility in methanesulfonic acid.

Methanesulfonic acid, 48 g (0.5 mole), and 14.2 g (0.1 mole) phosphorus pentoxide are stirred at 80°–90° C. until solution is effected. The solution is cooled to about 30° C., and 9.0 g (0.053 mole) diphenyl ether is added followed by 4.0 g (0.024 mole) terephthalic acid which has been ground and sifted through a 325-mesh screen. After heating for 3 hours at 100° C. all the terephthalic acid has reacted, the diketone product precipitating as it forms. The mixture is cooled to room temperature and filtered to collect the diketone which is then washed with methanesulfonic acid and water.

EXAMPLE 5

This example illustrates the preparation and purification of a mixture of diacid, keto-acid, and diketone suitable for polymerization to polyketone.

Phosphorus pentoxide, 14.2 g (0.1 mol), is added to 192 g (2 mol) methanesulfonic acid. The mixture is warmed and stirred until the phosphorus pentoxide dissolves. 4,4′-Oxydibenzoic acid, 13 g (0.05 mol), is added and the mixture is heated to 120° C. with stirring for 30 minutes. After cooling to room temperature, 8.5 g (0.05 mol) diphenyl ether is added. After stirring 1 hour at room temperature, most of the diacid has reacted to give roughly equal amounts of keto-acid and diketone with small amounts of higher oligomer. The reaction mixture containing a large amount of precipitate is poured into 400 mL water with stirring. The precipitate is collected and washed thoroughly with water. The mixture of diacid, keto-acid, and diketone thus obtained is purified by recrystallization from diphenyl ether to remove "ortho" isomers. Washing the filter cake with acetone removes residual diphenyl ether. When the amount of each component is determined by high pressure liquid chromatography (HPLC), the amount of diacid needed to balance the stoichiometry for polymerization may be determined.

EXAMPLE 6

This example illustrates the preparation and isolation of a keto-acid.

The procedure of Example 5 is followed. The mixture of diacid, keto-acid, and diketone is placed in a 500-mL flask along with 300 mL methylene chloride, 11.9 g (0.1 mole) thionyl chloride, and 0.1 g benzyltriethylammonium chloride. The mixture is refluxed with stirring for 3 hours, cooled and filtered. Diketone is in the filter cake; acid chlorides are in the filtrate. Methylene chloride is distilled from the filtrate at arm pressure. Afterwards the pressure is reduced and 4,4'-oxydibenzoyl chloride is removed by distillation. The undistilled keto-acid, 4-[4-(4-phenoxybenzoyl)phenoxy]benzoyl chloride, is purified by recrystallization.

The invention has been described in detail with particular reference to preferred embodiments thereof, but it will be understood that variations and modifications can be effected within the spirit and scope of the invention.

We claim:

1. A process for producing a diketone compound comprising
   contacting
   (A) at least one aromatic dicarboxylic acid containing 8 to 30 carbon atoms, wherein said aromatic dicarboxylic acid is
   (I) a compound of the formula

HOOC—R²13 COOH wherein R² is
   (a) a phenylene moiety optionally substituted with up to three substituents selected from the group consisting of lower alkyl, lower alkoxy, halo, hydroxy, acyl, perfluoroalkyl, cyano, nitro, dialkylamino, and acylamino,
   (b) a naphthylene moiety optionally substituted with up to six substituents selected from the group consisting of lower alkyl, lower alkoxy, halo, hydroxy, acyl, perfluoroalkyl, cyano, nitro, dialkylamino, and acylamino, or
   (c) a biphenylene moiety optionally substituted with up to eight substituents selected from the group consisting of lower alkyl, lower alkoxy, halo, hydroxy, acyl, perfluoroalkyl, cyano, nitro, dialkylamino, and acylamino;
   and wherein the —COOH moieties are directly bonded to an aromatic ring and are separated from each other by at least three carbon atoms; or
   (II) a compound of the formula

HOOC—R²—Y—R²—COOH wherein Y is a direct bond,

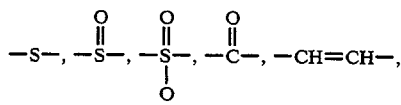

and each R², independently, is as defined hereinabove, with
   (B) at least one polynuclear aromatic compound containing 10 to 30 carbon atoms,
   in the presence of at least one solvent, phosphorus pentoxide, and at least a catalytic amount of at least one alkylsulfonic acid containing 1 to 4 carbon atoms, under conditions to promote formation of the desired diketone,
   said conditions comprising a molar ratio of reactant A to reactant B from of about 1 to 2.

2. The process of claim 1 wherein reactant (A) is selected from the group consisting of terephthalic acid, chloroterephthalic acid, 5-methylisophthalic acid, isophthalic acid, 4,4'-biphenyldicarboxylic acid, 4,4'-stilbenedicarboxylic acid, 4,4'-oxydibenzoic acid, 1,3-naphthalenedicarboxylic acid, 1,5-naphthalenedicarboxylic acid, 1,6-naphthalenedicarboxylic acid, 1,7-naphthalenedicarboxylic acid, 2,5-naphthalenedicarboxylic acid, 2,6-naphthalenedicarboxylic acid, and 2,7-naphthalenedicarboxylic acid.

3. The process of claim 1 wherein reactant (B) is
(I) a compound of the formula

H—R¹—X—R¹—H wherein
each R¹ is, independently,
   (a) a phenylene moiety optionally substituted with up to three substituents selected from the group consisting of lower alkyl and lower alkoxy,
   (b) a naphthylene moiety optionally substituted with up to six substituents selected from the group consisting of lower alkyl and lower alkoxy, or
   (c) a biphenylene moiety optionally substituted with up to eight substituents selected from the group consisting of lower alkyl and lower alkoxy;
X is a direct bond, O, S, or —CH=CH—; or
(II) a compound of the formula

H—R³—H wherein R³ is a polynuclear hydrocarbon moiety.

4. The process of claim 1 wherein reactant (B) is selected from the group consisting of diphenyl ether, dibenzofuran, diphenyl sulfide, biphenyl, naphthalene, anthracene, dibenzo-p-dioxin, fluorene, xanthane, and phenanthrene.

5. The process of claim 1 wherein a diketone compound is produced which is followed by the additional step of reacting the diketone with a diacid halide under conditions that promote formation of a polyketone.

6. The process of claim 1 wherein said alkylsulfonic acid is methanesulfonic acid.

7. The process of claim 1 wherein said alkylsulfonic acid catalyst also is the solvent.

8. The process of claim 7 wherein reactant (B) functions as a portion of the solvent.

9. The process of claim 1 carried out at a temperature of about 0° to 165° C.

10. The process of claim 1 carried out at a temperature of about 60° to 75° C.

11. The process of claim 1 wherein there is about a 5 to 10% stoichiometric excess of reactant (B) relative to reactant (A).

12. The process of claim 1 wherein the catalytic amount of alkylsulfonic acid is at least about 20 mole % of reactant (A).

13. The process of claim 1 wherein the amount of phosphorus pentoxide is about 1.5 to about 2.5 moles per mole of diacid.

14. The process of claim 1 having a reaction time of at least about 2 hours.

15. The process of claim 1 wherein reactant (A) is less than 5 weight % soluble in said alkylsulfonic acid and wherein reactant (A) is in finely divided form so that it will pass through a greater than or equal to 250 mesh screen.

16. The process of claim 1 including the additional step of purifying said diketone or keto-acid compound.

17. The process of claim 16 wherein the purifying step is carried out by recrystallization, distillation or a mixture thereof.

18. The process of claim 17 including the additional steps of recovering and recycling any remaining alkylsulfonic acid, organic anhydride compound, or mixture thereof.

19. A process for producing a diketone or keto-acid compound comprising contacting (A) at least one compound selected from the group consisting of terephthalic acid, chloroterephthalic acid, 5-methylisophthalic acid, isophthalic acid, 4,4'-biphenyldicarboxylic acid, 4,4'-stilbenedicarboxylic acid, 4,4'-oxydibenzoic acid, 1,3-naphthalenedicarboxylic acid, 1,5-naphthalenedicarboxylic acid, 1,6-naphthalenedicarboxylic acid, 1,7-naphthalenedicarboxylic acid, 2,5-naphthalenedicarboxylic acid, 2,6-naphthalenedicarboxylic acid, and 2,7-naphthalenedicarboxylic acid with (B) at least one compound selected from the group consisting of diphenyl ether, diphenyl sulfide, dibenzofuran, biphenyl, naphthalene, anthracene, dibenzo-p-dioxin, fluorene, xanthane, and phenanthrene in the presence of at least one solvent, phosphorus pentoxide, and at least a catalytic amount of at least one alkylsulfonic acid containing one to four carbon atoms, at a temperature of about 0° to 100° C. for a time sufficient to form the desired diketone or keto-acid compound.

20. The process of claim 19 wherein both the solvent and alkylsulfonic acid are methanesulfonic acid.

21. The process of claim 20 wherein the amount of reactant (B) is about a 5 to 10% stoichiometric excess relative to reactant (A), the amount of phosphorus pentoxide is about 1.5 to 2.5 moles of phosphorus pentoxide per mole of reactant (A), and wherein said process is carried out at about 60° to 70° C. for at least about 2 hours.

22. The process of claim 19 wherein reactant (A) is less than 5 weight % soluble in said alkylsulfonic acid and wherein reactant (A) is in finely divided form so that it will pass through a greater than or equal to 250 mesh screen.

* * * * *

UNITED STATES PATENT AND TRADEMARK OFFICE
CERTIFICATE OF CORRECTION

PATENT NO. : 5,338,881

DATED : August 16, 1994

INVENTOR(S) : Theodore R. Walker, Jr., et al

It is certified that error appears in the above-indentified patent and that said Letters Patent is hereby corrected as shown below:

Column 11, line 41 (Claim 1, line 9), "13" should be "—".

Column 12, line 5 (Claim 1, line 72), "⏐" should be "⏐⏐".

Signed and Sealed this

Eighteenth Day of October, 1994

Attest:

BRUCE LEHMAN

*Attesting Officer*       *Commissioner of Patents and Trademarks*